United States Patent [19]

Knudsen et al.

[11] 4,284,830
[45] Aug. 18, 1981

[54] MONOHALOGENATION OF SUBSTITUTED PHENOL

[75] Inventors: Ronald D. Knudsen; Darryl R. Fahey, both of Bartlesville, Okla.

[73] Assignee: Phillips Petroleum Co., Bartlesville, Okla.

[21] Appl. No.: 117,747

[22] Filed: Feb. 1, 1980

[51] Int. Cl.$^3$ .................. C07C 39/26; C07C 39/28
[52] U.S. Cl. ................................ 568/779; 568/726; 568/744; 568/774
[58] Field of Search ............... 568/779, 774, 726, 743, 568/744

[56] References Cited

U.S. PATENT DOCUMENTS

| | | | |
|---|---|---|---|
| 2,778,857 | 1/1957 | Beman et al. | 568/779 |
| 3,546,302 | 12/1970 | Asadorian et al. | 568/779 |
| 3,996,291 | 12/1976 | Dietrich et al. | 568/779 |

FOREIGN PATENT DOCUMENTS 52-27734  2/1977  Japan ....................... 568/779

Primary Examiner—Werren B. Lone

[57] ABSTRACT

Monohalogenated hydrocarbyl substituted phenols can be produced by reacting hydrocarbyl substituted phenols with a halogen carrying out the reaction in a diluent such as benzene, alkyl substituted benzenes, and halosubstituted hydrocarbons of 1–3 carbon atoms.

6 Claims, No Drawings

MONOHALOGENATION OF SUBSTITUTED PHENOL

This invention relates to the production of monohalo substituted and hydrocarbyl substituted phenols.

BACKGROUND OF THE INVENTION

Chlorinated substituted phenols are well known materials. These compositions are useful by themselves or as intermediates for the production of insecticides and herbicides. The synthesis of such compositions is widely reported. Generally the production involves the reaction of the substituted phenol with the halogen. In general, however, such a reaction results in products which are mixtures of mono-, di- and polyhalogenated phenols. These mixtures sometimes are difficult to separate.

Furthermore, the reactions frequently involve long reaction times.

STATEMENT OF THE INVENTION

It is therefore one object of this invention to provide a process for the production of monohalo substituted and hydrocarbyl monohalo substituted phenols which is both technically and economically advantageous.

Another object of this invention is to provide such a process which results in the monohalogenated hydrocarbyl substituted phenol with high selectivities.

Other objects, features, details, advantages, and embodiments of this invention will become apparent from the following detailed description of the invention and the appended claims.

In accordance with this invention it has now been found that certain hydrocarbyl substituted phenols can be monohalogenated by reacting these phenols with halogen in the presence of specifically defined diluents.

STARTING MATERIALS

Hydrocarbyl substituted phenols useful in accordance with this invention for the halogenation process are generally represented by the formula

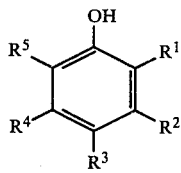

wherein the radicals R can be hydrogen, alkyl, cycloalkyl or aryl radicals having 1 to 10 carbon atoms. At least one of the radicals R has to be hydrogen. The preferred substituted phenols under this formula have 7 to 10 carbon atoms. The halogenation in ortho and para position is presently preferred. Thus, one of the radicals $R^1$, $R^3$, and $R^5$ preferably is hydrogen; in other words when $R^3$ is a hydrocarbyl radical $R^1$ and/or $R^5$ are a hydrogen atom and when $R^1$ and/or $R^5$ are hydrocarbyl radicals, $R^3$ is a hydrogen atom, in the preferred group of substituted phenols.

The most preferred class of monohydrocarbyl substituted phenols encompasses the p-alkyl phenols, and in particular those in which the alkyl group is bound via a tertiary carbon atom to the aromatic hydrocarbon of the phenol ring.

Examples for the substituted phenols that are useful in accordance with this invention are:

2, 3, or 4-methylphenol
2, 3, or 4-ethylphenol
2, 3, or 4-propylphenyl
2, 3, or 4-isopropylphenol
2, 3, or 4-n-butylphenol
2, 3, or 4-sec-butylphenol
2, 3, or 4-iso-butylphenol
2, 3, or 4-tert-butylphenol
2, 3, or 4-hexylphenol
2, 3, or 4-decylphenol
2, 3, or 4-cyclohexylphenol
2, 3, or 4-phenylphenol
2,3; 2,4; 2,6; or 3,5-dimethylphenol
2,3; 2,4; 2,6; or 3,5-diethylphenol
2,3; 2,4; 2,6; or 3,5-dipropylphenol
2,3; 2,4; 2,6; or 3,5-dibutylphenol
2,3; 2,4; 2,6; or 3,5-dihexylphenol
2,3; 2,4; 2,6; or 3,5-didecylphenol
2,3; 2,4; 2,6; or 3,5-dicyclohexylphenol
2,3; 2,4; 2,6; or 3,5-diphenylphenol
2,3,4; 2,3,5; or 3,4,5-trimethylphenol
2,3,4; 2,3,5; or 3,4,5-tributylphenol
2,3,4; 2,3,5; or 3,4,5-tridecylphenol
2,3,4; 2,3,5; or 3,4,5-tricyclohexylphenol
2,3,4; 2,3,5; or 3,4,5-triphenylphenol The halogens suitable in this invention are chlorine, bromine and iodine. Chlorine and bromine are presently preferred since these halogens provide more active compositions for use as intermediates. The halogen can be added in liquid or gaseous phase and can be admixed with inert diluents or gases such as nitrogen. The mole ratio of halogen to substituted phenol generally is from 0.5:1 to 1.5:1.

DILUENT

In accordance with this invention it has been found that the halogenation reaction contemplated results in a particularly high selectivity for the desired halogen substituted hydrocarbyl phenol when specific non-polar diluents or solvents are utilized. These non-polar diluents can be defined generically by their properties, namely that they are non-polar, that they exhibit some solubility with the substituted phenol, that they are inert to the action of the halogen and that their dielectric constant is below about 11 at 20° C.

Two classes of diluents that have been found to be particularly efficient are the aromatic hydrocarbons and the lower halosubstituted alkenes or alkanes having up to 3 carbon atoms and up to 3 halogen atoms. More specifically the diluents preferred in accordance with this invention are benzenes and mono-, di- and trialkyl substituted benzenes of 7 to 9 carbon atoms, as well as the alkanes of 1 to 3 carbon atoms being substituted by 1 to 3 halogen atoms and the halogen being chlorine and/or bromine.

Specific examples for the diluents contemplated for the process of this invention include benzene, toluene, the xylenes, ethylbenzene, dichloromethane, 1,2-dichloroethane, 1,2-dichloroethylene, trichloroethylene, 1,2-dibromoethane, tribromoethylene.

The weight ratio of diluent to substituted phenol is of influence on the rate of reaction and probably on the product selectivity in the process of this invention. Generally, the less diluent employed, the faster the reaction proceeds and less heat is dissipated from the reaction zone by the diluent. Generally, it is contemplated to employ at least enough diluent to provide some liquid phase. Thus, solid slurries are within the scope of this invention. More specifically and advantageously, however, a higher amount of diluent is utilized and the weight ratio of the diluent to the substituted phenol will be defined as follows:

Broad range: 20:1 to 0.5:1
Preferred range: 5:1 to 1:1

REACTION CONDITIONS

The reaction conditions for the process of this invention are not overly critical. Generally, the temperature and pressure will be in the following ranges:

Temperature: 0° C. to 100° C.
Pressure: 0 psi to 100 psi (0–0.7 MPa)

The time of the reaction can be chosen in broad ranges and will be primarily dependent upon the reactant concentration as well as the other reaction conditions. The reaction times will generally be between 0.1 hour and 12 hours.

The following examples illustrate further preferred details of this invention but are not intended to unduly limit the scope thereof.

EXAMPLE I

This example is an inventive run employing a non-polar diluent at a diluent to substituted phenol weight ratio of 7:1. The results show good conversion and product selectivity.

Into a 1000 milliliter three neck weighed flask fitted with a magnetic stirrer, gas dispersion tube, and thermometer and wrapped with aluminum foil to exclude light was charged 100 grams (0.666 moles) of 4-tert-butylphenol dissolved in 700 milliliters (606.8 grams) of toluene. Chlorine was slowly bubbled through the dispersion tube as the temperature rose to 28° C. After 11 hrs., a yellow color appeared and a weight increase of 37.4 grams (47.3 grams are theoretical) was recorded. An aliquot was removed and analyzed by GLC employing a 182.9 cm (6 foot)×0.476 cm (3/16 inch) column packed with Carbowax 20M. A 100% conversion of the starting material was noted with an 84% selectivity to 4-tert-butyl-2-chlorophenol.

The toluene solution was water washed and allowed to evaporate at ambient room temperature. The remaining residual material was distilled on a spinning band column at 46° C./0.1 torr (mm Hg) and a reflux ratio of 20:1. A front fraction of 22.2 grams contained 18.3 grams product (82% purity). Purity was measured on a 182.88 cm (6 foot)×0.476 cm (3/16 inch) column of OV-210 on 100/120 Chromosorb P programmed from 100° to 200° C. at 16°/min. using a thermal conductivity detector. The remaining 82.2 grams (67 mole % yield) then distilled with 99+% purity.

EXAMPLE II

This example is an inventive run employing the same non-polar diluent as used in Example I but at a lower diluent to phenol weight ratio, namely 1.7:1. The results also show good conversion and product selectivity and the reaction time is reduced from about 11 hours to 30 minutes. The reaction temperature is slightly higher (28° C. vs. 58° C.) than in Example I, probably due to faster chlorine addition and less dilution.

Into a 1000 milliliter three neck flask equipped with a mechanical stirrer, a Friedrich Condensor vented to a funnel inverted over water, thermometer, and a gas-dispersion tube was charged 100 grams (0.666 moles) of 4-tert-butylphenol and 200 milliliters (173.4 grams) of toluene. Although less than half of the phenol dissolved, the mixture was easily stirred as a suspension. Four minutes after chlorine and stirring was begun, the phenol had completely dissolved and the temperature had risen to 58° C. The chlorine addition was controlled to maintain the temperature between 50°-60° C. After 16 minutes the conversion was 60% and after a total of 30 minutes the conversion was 100% with a 94% selectivity to 4-tert-butyl-2-chlorophenol. Distillation of the reaction mixture afforded 102 grams of liquid distilling from 172°-191° C./200 torr (mm Hg) comprised of 98.6 wt. % of 4-tert-butyl-2-chlorophenol, 0.2 wt. % toluene, and 1.2 wt. % of the oxidation product of 4-tert-butyl-2-chlorophenol; therefore, the distilled product yield is 100.6 grams (81.8 wt. % of theoretical). The residue weighed 8.8 grams and was 28% 4-tert-butyl-2-chlorophenol.

EXAMPLE III

This example is an inventive run employing another non-polar diluent, dichloromethane. The run described in Example II was repeated except dichloromethane was used in place of toluene. After 26 minutes of chlorination time there was an 85% conversion of phenol and after a total of 37 minutes there was a 100% conversion. GLC analysis indicated a 93% selectivity to 4-tert-butyl-2-chlorophenol. The mixture was washed twice with 70 milliliter portions of water, dried over anhydrous MgSO₄ and distilled to give 105.3 grams (85.6% of theoretical) of 4-tert-butyl-2-chlorophenol having 98.6% purity.

EXAMPLE IV

This example is a control run and shows low conversion when the chlorination of 4-tert-butylphenol is conducted in a polar diluent.

To a three neck flask equipped as herein described was charged 10 grams (0.0666 moles) of 4-tert-butylphenol and 135grams of water. This is a 13.5/1 wt. ratio of diluent to phenol. About 4.3 grams of chlorine was bubbled into the stirred mixture within 1 hour while the temperature rose from about 25° C. to 33° C. The mixture was stirred for another 45 minutes without additional chlorine being added. Analysis of an ether extract of the reaction mixture indicated a 30 wt. % conversion and a 94% selectivity of 2,4,6-trichloro-4-tert-butylcyclohex-2,5-dienone although the exact identity was questionable.

This run was repeated using a mixture of 65 grams water and 59.4 grams (75 milliliters) methyl alcohol. This is a 12.4/1 wt. ratio of diluent to phenol. The final reaction temperature was 53° C. Analysis of an aliquot sample indicated a 40% conversion with a 96% selectivity to a product where identity was assumed, but not verified, to be 4-tert-butyl-2-chlorophenol.

The run was again repeated using a different weight ratio of water to methyl alcohol, namely 50 grams of water and 79.2 grams (100 milliliters) of methyl alcohol. This is a 12.9/1 wt. ratio of diluent to phenol. The final reaction temperature was 51° C. Analysis of an aliquot sample indicated a 93-97% conversion with about a 76% product selectivity. The major product was identified as 2,4,6-trichloro-4-tert-butylcyclohex-2,5-dienone.

The results herein disclosed are summarized in Table I and show that 4-tert-butylphenol can be converted to 4-tert-butyl-2-chlorophenol in higher conversions and high selectivity when the reaction is carried out in a non-polar diluent rather than a polar diluent. The time to complete the reaction to the desired product is greatly affected by the rate of chlorine addition.

TABLE I

Chlorination of 4-Tert-Butylphenol to 4-Tert-Butyl-2-Chlorophenol

| Example No. | Diluent | Wt. Ratio Diluent/Phenol | Reaction Conditions Temp. °C. | Time, Hrs. | % Conversion | % Selectivity[a] |
|---|---|---|---|---|---|---|
| I | Toluene | 6.07/1 | 28 | 11.0 | 100 | 84 |
| II | Toluene | 1.70/1 | 50-60 | 0.5 | 100 | 94 |
| III | Dichloromethane | 1.70/1 | 40 | 0.5 | 100 | 93 |
| IVa | Water | 13.5/1 | 33 | 1-2 | 30 | 94[b] |
| IVb | 52 Wt. % Water- 48 Wt. % Methyl Alcohol | 12.4/1 | 53 | 1-2 | 40 | 96[b] |
| IVc | 38 Wt. % Water- 62 Wt. % Methyl Alcohol | 12.9/1 | 51 | 1-2 | 93-97 | 76[c] |

[a] 4-Tert-Butyl-2-Chlorophenol
[b] Product identity questionable
[c] Major product is 2,4,6-trichloro-4-tert-butylcyclohex-2,5-dienone The results shown in the above table clearly demonstrate the advantageous features of this invention as compared to similar runs utilizing water or a water/methyl alcohol mixture as the diluent instead of the toluene or dichloromethane.

Reasonable variations and modification which will become apparent to those skilled in the art can be made in this invention without departing from the spirit and scope thereof.

We claim:

1. A process for producing a mono-halogenated hydrocarbyl substituted phenol which comprises reacting a hydrocarbyl substituted phenol having the formula

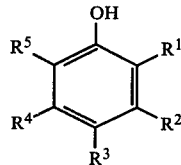

wherein $R^1$, $R^2$, $R^3$, $R^4$, and $R^5$ are hydrogen, alkyl, cycloalkyl, or aryl radicals having 1 to 10 carbon atoms with the further provision that at least one of the radicals $R^1$ to $R^5$ is a hydrocarbyl radical, wherein at least one of the radicals, R has to be hydrogen, with a halogen selected from the group consisting of chlorine, bromine and iodine in the presence of a non-polar diluent selected from the group consisting of benzene, mono-, di- and trialkyl substituted benzenes having 7 to 10 carbon atoms and halosubstituted hydrocarbons having 1 to 3 carbon atoms and 1 to 3 halogen atoms selected from the group consisting of chlorine and/or bromine the mole ratio of halogen to phenol being in the range of 0.5:1 to 1.5:1, and separating the monohalohydrocarbyl phenol from the reaction mixture obtained in the reaction step.

2. A process in accordance with claim 1 wherein said hydrocarbyl substituted phenol is a p-alkylphenol, said halogen is chlorine or bromine and said diluent is toluene or dichloromethane.

3. A process in accordance with claim 1 wherein the weight ratio of said non-polar diluent employed to said hydrocarbyl substituted phenol is in the range of 5:1 to 1:1.

4. A process in accordance with claim 1 wherein the mole ratio of halogen to hydrocarbyl substituted phenol is in the range of 0.5:1 to 1.5:1.

5. A process in accordance with claim 1 wherein said halogenation reaction is carried out essentially in the absence of visible light.

6. A process in accordance with claim 1 wherein 4-tert-butylphenol and chlorine are reacted in the presence of toluene or dichloromethane.

* * * * *